United States Patent
Leybovich

(10) Patent No.: US 6,494,098 B1
(45) Date of Patent: Dec. 17, 2002

(54) METHOD OF ULTRASONIC ON-LINE TEXTURE CHARACTERIZATION

(75) Inventor: Alexander Leybovich, Hilliard, OH (US)

(73) Assignee: Tosoh SMD, Inc., Grove City, OH (US)

(*) Notice: Subject to any disclaimer, the term of this patent is extended or adjusted under 35 U.S.C. 154(b) by 0 days.

(21) Appl. No.: 09/600,039

(22) PCT Filed: Jan. 5, 1999

(86) PCT No.: PCT/US99/00091

§ 371 (c)(1),
(2), (4) Date: Jul. 10, 2000

(87) PCT Pub. No.: WO99/36769

PCT Pub. Date: Jul. 22, 1999

Related U.S. Application Data

(60) Provisional application No. 60/071,754, filed on Jan. 16, 1998.

(51) Int. Cl.[7] .............................................. G01N 29/00
(52) U.S. Cl. ........................... 73/620; 73/579; 73/588; 73/597; 73/616
(58) Field of Search .................... 73/597, 602, 598, 73/616, 620, 600, 579, 629, 584, 588, 615

(56) References Cited

U.S. PATENT DOCUMENTS

| | | | |
|---|---|---|---|
| 4,899,589 A | * | 2/1990 | Thompson et al. ............ 73/597 |
| 5,048,340 A | * | 9/1991 | Thompson et al. ............ 73/597 |
| 5,251,486 A | * | 10/1993 | Thompson et al. ............ 73/597 |
| 5,404,754 A | * | 4/1995 | Wang .......................... 73/602 |
| 5,406,850 A | * | 4/1995 | Bouchard et al. ............. 73/620 |
| 5,631,424 A | * | 5/1997 | Nieters et al. ................ 73/598 |
| 5,693,203 A | * | 12/1997 | Ohhashi et al. ........ 204/298.12 |
| 5,804,727 A | * | 9/1998 | Lu et al. ........................ 73/597 |
| 6,269,699 B1 | * | 8/2001 | Gilman et al. ................ 73/601 |

FOREIGN PATENT DOCUMENTS

| EP | WO 01/086282 | * 11/2001 |
|---|---|---|

OTHER PUBLICATIONS

F. Wagner and H.J. Bunge, Low Resolution Texture Analysis, in *Advances and Application of Quanitative Texture Analysis* ed. H.J. Bunge and C. Esling, Informationgesellschaft Verlag, 1991, 147.

(List continued on next page.)

*Primary Examiner*—Hezron Williams
*Assistant Examiner*—Jacques Saint Surin
(74) *Attorney, Agent, or Firm*—Wegman, Hessler & Vanderburg

(57) ABSTRACT

A sputtering target (24) under test is irradiated with an ultrasonic pulse (20). The ultrasonic pulse (20) has a wavelength in the sputtering target (24) in the range of the average grain size for the target (24) under test. Backscattering echoes (28) are produced by the interaction of the pulse (20) with grain boundaries in the target (24) under test. The backscattering echoes (28) are detected and a representative electrical signal is generated. The number of occurrences of the backscattering echoes (28) having amplitudes within predetermined ranges are determined. A histogram of the number of occurrences versus amplitude is plotted. The histogram for the target (24) under test is compared with reference histograms for sputtering targets having known crystallographic orientations to determine the texture of the target (24) under test.

6 Claims, 12 Drawing Sheets

OTHER PUBLICATIONS

H–J Kopinech, and H. Otten, Industrial Application of On–Line Texture Measurement, in *Advances and Application of Quanitative Texture Analysis* ed. H.J. Bunge and C. Esling, Informationesellschaft Verlag, 1991, 153.

M. Spies and E. Schneider, Nondestructive Analysisi of the Deep–Drawn Behaviour of Rolled Sheets with Ultrasonic Techniques, in *Advances and Application of Quanitative Texture Analysis* ed. H.J. Bunge and C. Esling, Informationesellschaft Verlag, 1991, 167.

Mason et al., "Energy Losses of Sound Waves in Metals Due to Scattering and Diffusion", *Journal of Applied Physics*, vol. 10, Oct. 1948, pp. 940–946.

Elbaum et al., "Ultrasonic Methods in Solid State Physics", *NY Academic Press*, 1969, pp. 77–86.

Goebbels, "Materials Characterization for Process Control and Product Conformity", 1994, pp. 132, 133.

Cullity, "Elements of X–Ray Diffraction", 1978, pp. 295–300.

\* cited by examiner

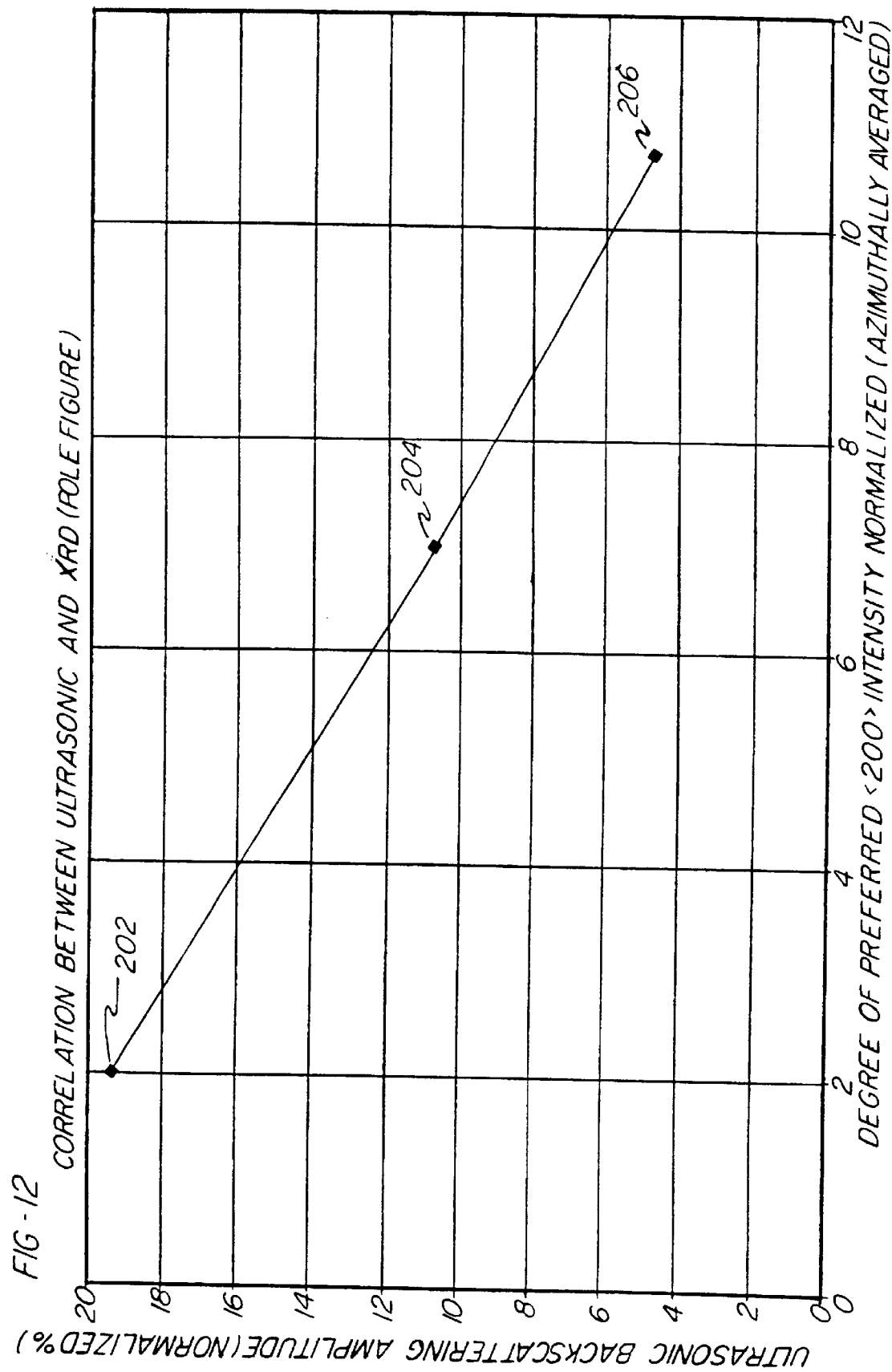
FIG-12 CORRELATION BETWEEN ULTRASONIC AND XRD (POLE FIGURE)

METHOD OF ULTRASONIC ON-LINE TEXTURE CHARACTERIZATION

This application claims the benefit of Provisional application Ser. No. 60/071,754, filed Jan. 16, 1998.

BACKGROUND OF THE INVENTION

This invention relates to a non-destructive testing method for determining the texture of materials using ultrasonics.

The word "texture" designates direction-dependent properties of materials. One direction-dependent property of particular interest is elastic anisotropy in polycrystalline materials that results from the non-random distribution of the crystallographic orientations of single grains. Crystallographic texture is described by an orientation distribution function (ODF). Information on ODF is usually obtained from pole figure X-ray diffraction and typically consists of thousands of diffraction data points.

Conventional texture analysis of materials normally involves destructive testing. A small sample is cut off from a material and tested in a laboratory. In some cases, especially in production control, it is not necessary to determine the "whole" texture. In this case, it is possible to use a low-resolution texture analysis method which relies upon a strict correlation between some material physical properties such as, for example, elastic or magnetic properties, and crystallographic texture. By restricting the texture analysis to a low-resolution technique, it is possible to perform texture analysis in a non-destructive way that offers the possibility of on-line quality control inspection.

Three different techniques for low-resolution texture analysis are known. A first technique consists of taking X-ray measurements of a material under test. A device, called an "On-Line Texture Analyzer", designed and used for this purpose, irradiates a sample with an incident beam containing a continuous spectrum of wavelengths such as, for example, the X-ray bremsstrahlung spectrum. Characteristic pole-intensities of the sample are measured by energy-dispersive detectors detecting the X-ray bremsstrahlung spectrum transmitted through the sample material. However, this technique is limited to relatively small thicknesses of material. This limitation is due to strong X-ray attenuation and dispersion inside the polycrystalline material, and strict requirements for positioning of the X-ray source and detectors with respect to the texture of the material sample.

A second technique consists of electromagnetic Barkhausen noise and dynamic magnetostriction measurements. However, this technique is limited to materials having strong magnetic anisotropy.

A third technique is based on the measurement of a material's vibrational properties, such as an ultrasound velocity, which are known to be correlated with the material texture. Ultrasound velocity measurements have advantages over the first two techniques in that samples to be tested are not limited in thickness, and materials without strong magnetic anisotropy may be analyzed.

A prior art ultrasonic method for low-resolution texture analysis of single-phase polycrystalline materials such as, for example, low-alloyed aluminum having a cubic structure and orthorhombic texture is depicted in FIG. 1. This technique employs a pulse-echo method to determine three ultrasound absolute propagation velocities (with respect to the specimen coordinate system) propagating in the rolling, transverse, and normal directions.

A single, short-duration, high-frequency ultrasound pulse 10, generated by an ultrasonic transducer 12, advances into a specimen 14 which has flat, parallel surfaces. Multiple reflections of ultrasound inside the specimen 14 results. A series of consecutive echos 16 (see FIG. 1A) with gradually decreasing amplitudes are generated. The echos 16 are received by the transducer 12 for calculation of the propagation velocity. The propagation velocity may be calculated using measurements of ultrasound round-trip path length and ultrasound round-trip time-of-flight. The round-trip path length may be determined as a doubled specimen thickness (L in FIG. 1) precisely measured in the direction of ultrasound propagation. The ultrasound time-of-flight may be measured as a time interval or period 17 between the leading edges of two consecutive echos 16. The absolute propagation velocities, calculated as a ratio of round-trip path length to time-of-flight, are usually used to determine the elastic constants (fourth-order expansion coefficients of the elasticity matrix) which characterize the texture of the specimen 14.

However, the accuracy of time-of-flight measurements may vary substantially depending on a number of factors such as: ultrasound pulse frequency spectrum; pulse rise time, length and shape; transducer-to-specimen positioning and coupling; and frequency band, resolution and accuracy of the electronic receiving system. The accuracy of the time-of-flight measurements is especially critical for materials having a low elastic anisotropy factor such as, for example, low-alloyed aluminum. In order to obtain acceptable measurement accuracy, out-of-line laboratory measurements may be required. The prior art ultrasonic method for texture characterization may not be suitable for on-line texture analysis.

SUMMARY OF THE INVENTION

A method of on-line ultrasonic texture characterization of a sputtering target is provided. Texture characterization may be accomplished through analysis of an ultrasonic backscattering signal amplitude distribution. A broad-band, focused ultrasonic transducer generates a megacycle center frequency ultrasonic pulse having a wavelength in the range of the average grain size (in the direction of ultrasound propagation) of a sputtering target specimen. The ultrasonic pulse is introduced into the specimen at an incident angle normal to the surface of the specimen. Due to interaction of the ultrasonic pulse with the texture of the specimen, backscattering echoes are generated in a portion of the specimen located within the transducer focal zone. The backscatter region extends at least one grain layer beneath the specimen surface to a depth of several grain layers in thickness. The backscattering echoes propagate back to the transducer where the echoes are converted by the transducer into an electrical signal which is processed by a broad-band acquisition system. A maximum amplitude value of the backscattering signal is extracted from the processed data and stored in a memory of the acquisition system for future data analysis. Data analysis is performed using data graphical representation in the form of a histogram of "occurrences versus amplitude" where the amplitude is plotted along the x axis while the occurrences (counts for certain amplitude values) are plotted along the y axis. The histogram is compared with histograms for reference standards having known preferred crystallographic and grain orientation, grain size, and chemical composition.

Therefore, it is an object of the invention to provide a method of ultrasonic on-line texture characterization.

It is a further object of the invention to provide a method of on-line texture characterization including the step of generating an ultrasonic pulse with a wavelength in the range of the average grain size of a specimen material in the direction of ultrasound propagation.

It is yet another object of the invention to provide a method of ultrasonic on-line texture characterization including the step of detecting an ultrasonic backscattering signal generated by interaction of an initial ultrasonic pulse with specimen material texture.

A still further object of the invention is to provide a method of ultrasonic on-line texture characterization including the step of plotting the backscattering signal amplitude in the form of a histogram of "occurrences versus amplitude", and comparing the histogram with similar histograms for materials having known preferred crystallographic and grain orientation, grain size, and chemical composition.

Other objects of the invention will be apparent from the following description the accompanying drawings and the appended claims.

BRIEF DESCRIPTION OF THE DRAWINGS

FIG. 1A is a schematic diagram showing the ultrasound echoes obtained by the prior art method shown in FIG. 1;

FIG. 12 shows the correlation between ultrasonic backscattering amplitude and degree of <200> preferred orientation for the sputtering targets and single crystal of FIGS. 4-11.

DETAILED DESCRIPTION OF THE PREFERRED EMBODIMENTS

Figure 2:
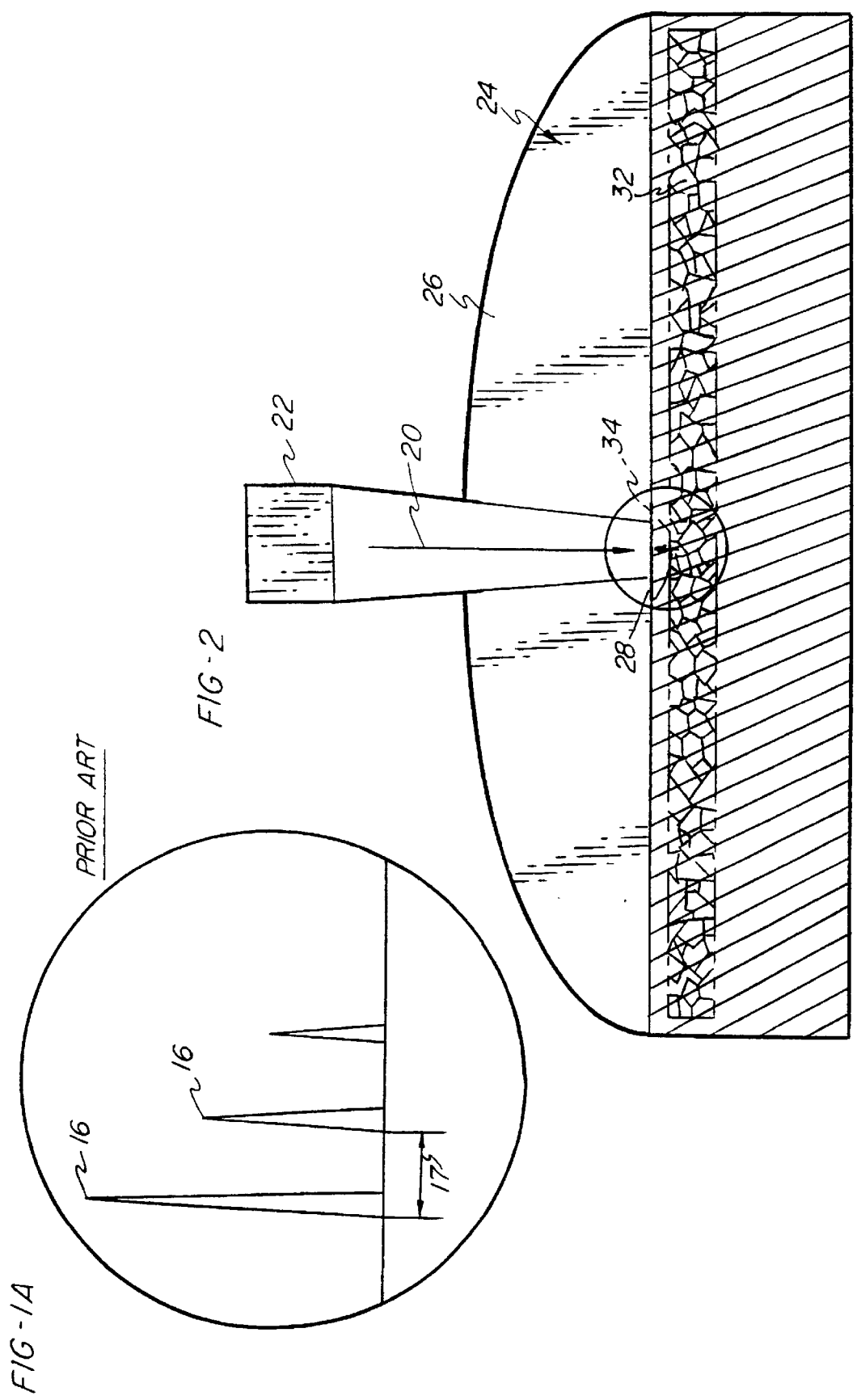
FIG. 2 is a schematic diagram of a method of ultrasonic on-line texture characterization in accordance with the invention.
Figure 3:
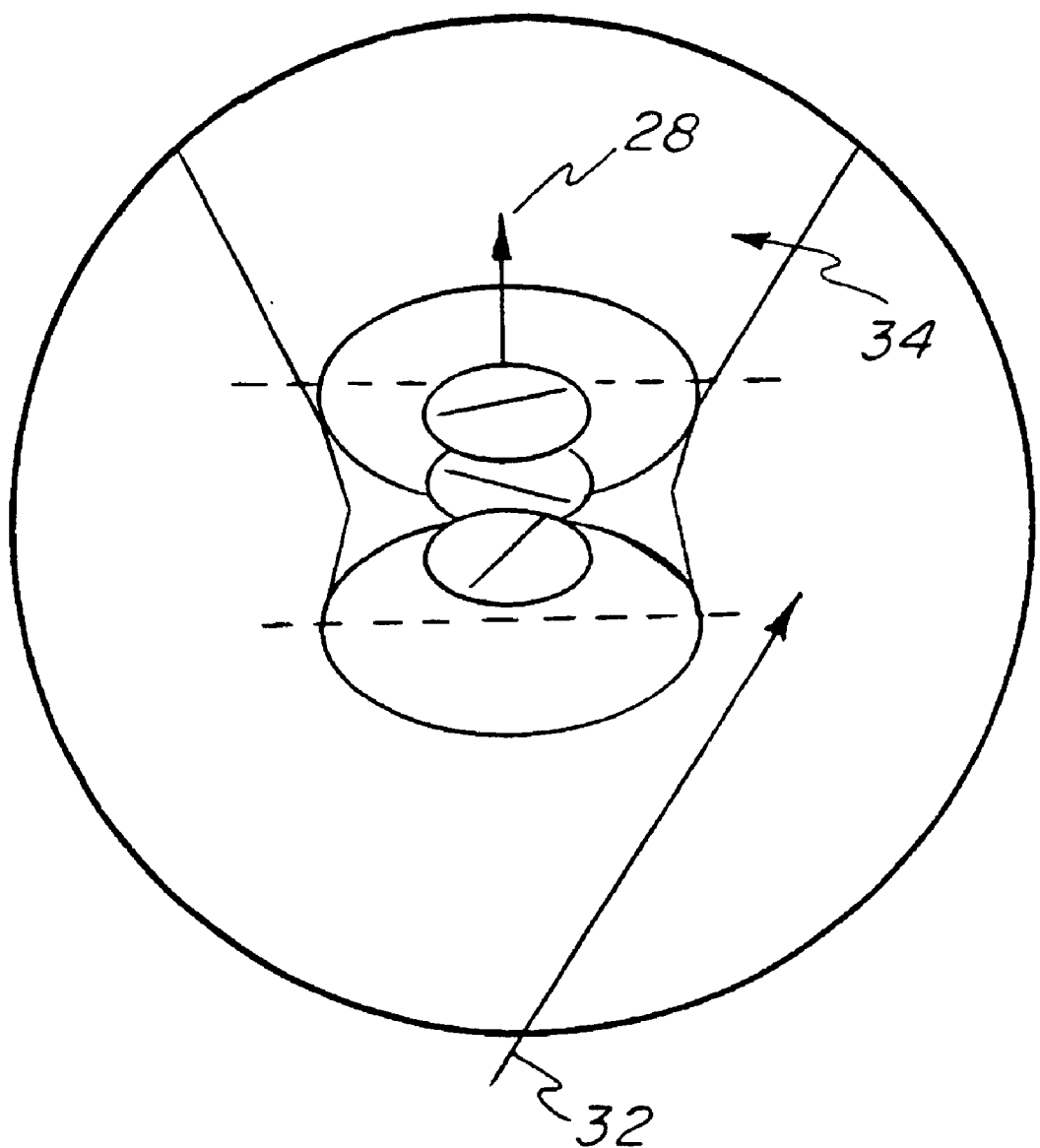
FIG. 3 is an enlarged schematic view of the backscattering region of the sputtering target of FIG. 2 showing backscattering echoes propagating from grain boundaries.

Turning to FIGS. 2 and 3, there may be seen schematic diagrams illustrating the method of the instant invention. A single, short-duration, megahertz frequency range ultrasonic pulse 20, is generated by a focused ultrasonic transducer 22. The pulse 20 is directed at a material 24 such that the angle of incidence of the pulse 20 is normal to the surface 26 of the material 24. A backscattering signal 28 originates in a backscattering region 32. The backscattering region 32 is located inside a transducer focal zone 34 and has a depth extending from at least one grain layer beneath the surface 26 to a depth of several grain layers.

Figure 1:
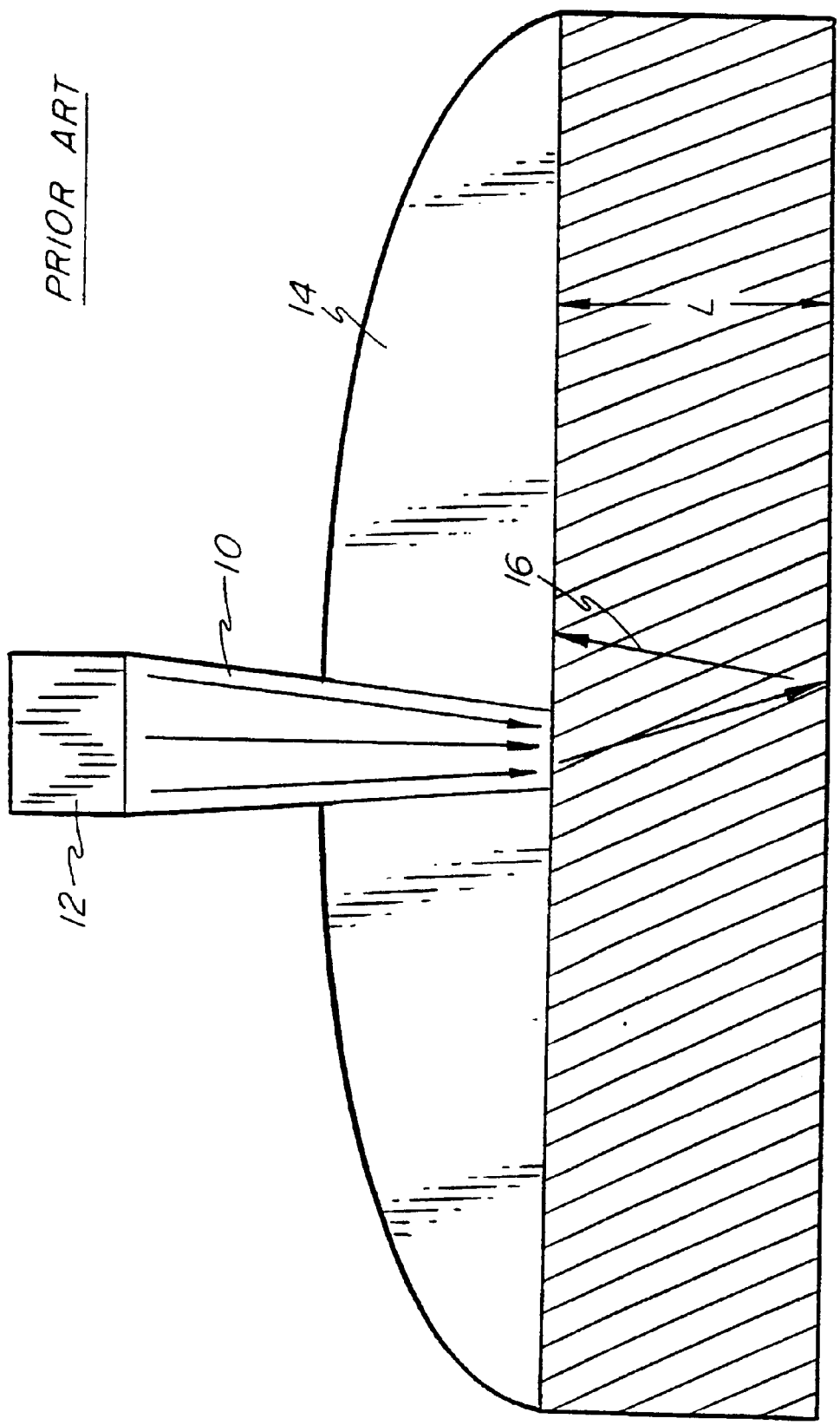
FIG. 1 is a schematic diagram of a prior art method of ultrasonic texture analysis.
Figure 6:
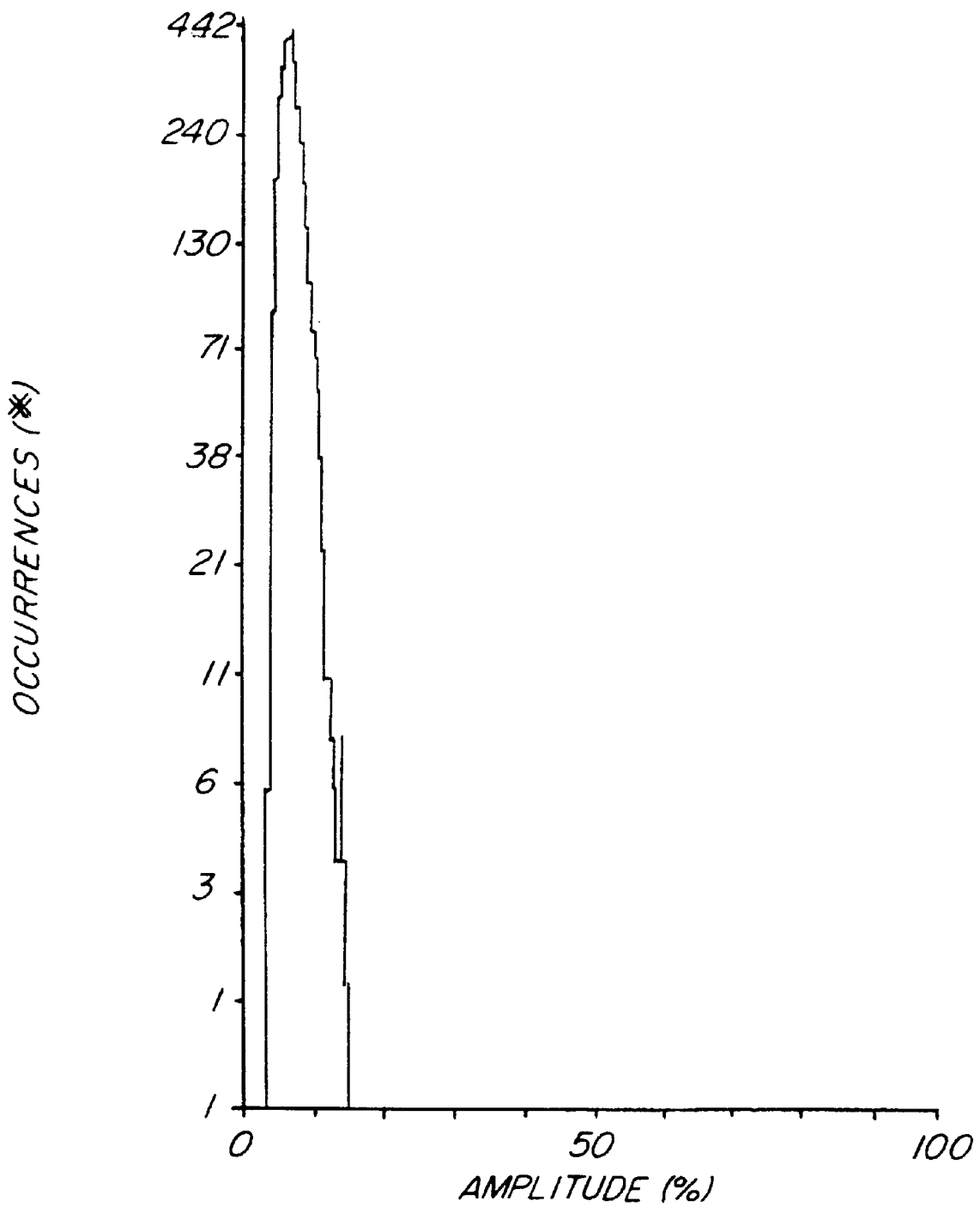
FIG. 6 is a histogram of "occurrences versus amplitude" obtained according to the method of the invention for an anisotropic material having a strong <100> preferred crystallographic orientation.

Backscattering occurs as a result of acoustic, impedance (i.e., ultrasound velocity) mismatch at grain boundaries of adjacent grains. Due to a limited number of grain boundaries along the ultrasound path inside the backscattering region 32, the backscattering signal 28 experiences less signal volume averaging than the reflected ultrasonic signal of the prior art (FIG. 1). At a nearly resonant mode of ultrasound propagation (i.e., the ultrasound wavelength is in the range of average grain size), the statistics of identical wave phase shift at the grain boundaries inside the backscattering region 32 will depend on the degree of preferred crystallographic orientation. The number of identical wave phase shifts increases with increasing degree of preferred crystallographic orientation. The increase in the number of identical phase shift occurrences is detected as an increase in the number of counts for identical backscattering amplitudes. As a result, a histogram of "occurrences versus amplitude" tends to shrink in width and stretch in height with increasing kurtosis of the histogram (FIG. 6). In contrast, for materials having more isotropic texture, the histogram of backscattering signal amplitude is broader and shorter due to more random phase shift distribution (FIG. 4).

Figure 4:
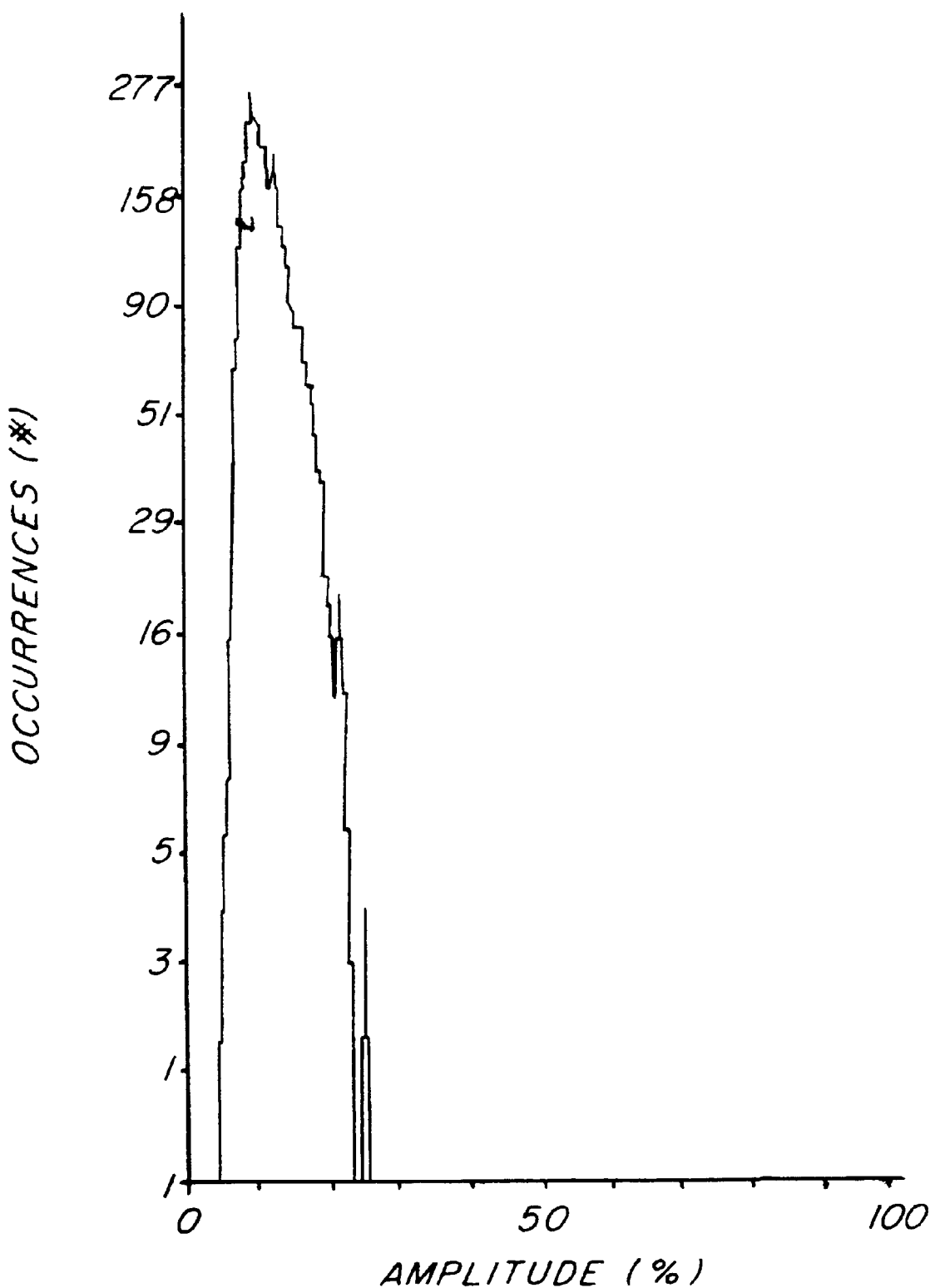
FIG. 4 is a histogram of "occurrences versus amplitude" obtained according to the method of the invention for a relatively isotropic "random" texture.

Turning now to FIGS. 4 and 6, there may be seen histograms of backscattering signal amplitudes obtained in accordance with the method of the invention for two different material specimens. The first material specimen used to produce the histogram given in FIG. 4 is of an isotropic random crystallographic orientation. The FIG. 6 histogram results from ultrasonic analysis, in accordance with the invention, of a strong <100> preferred crystallographic orientation.

Figure 5:
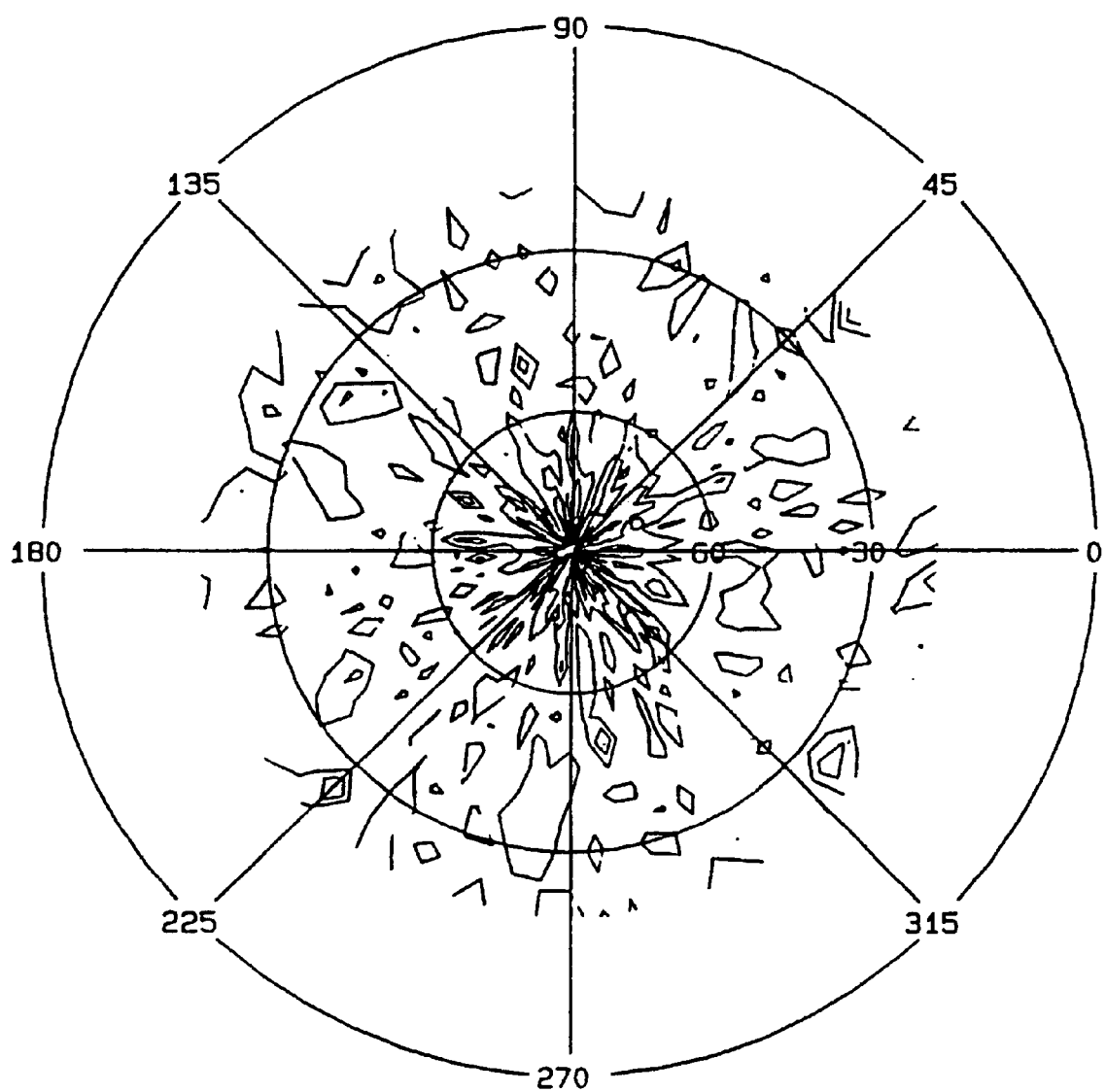
FIG. 5 is an X-ray diffraction pole-figure proof for the data shown in FIG. 4.
Figure 7:
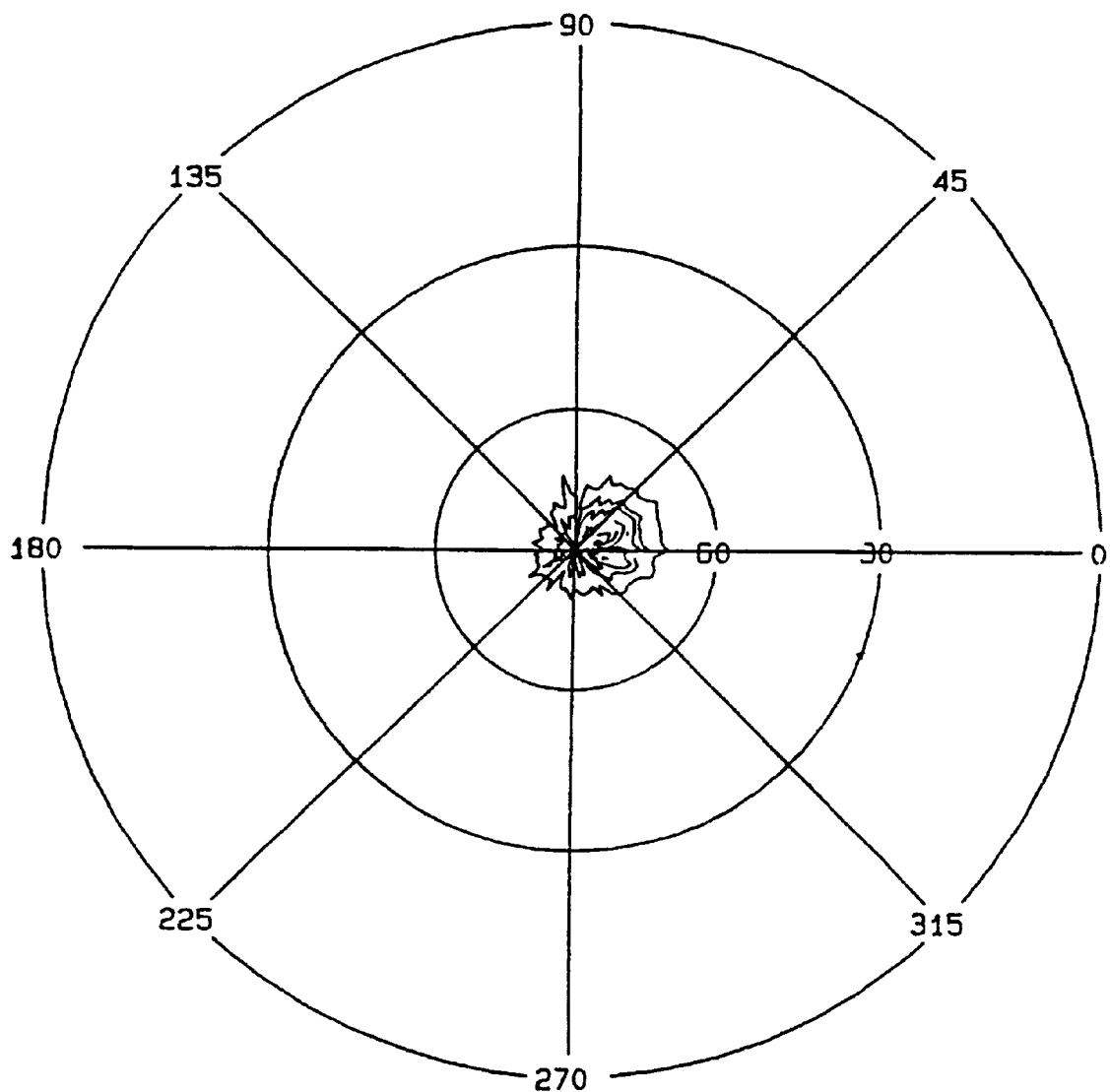
FIG. 7 presents the X-ray diffraction pole-figure proof for the data shown in FIG. 6.

In both cases, the specimen materials comprise aluminum-0.5 weight percent copper alloy having equivalent-axed grain texture (crystallographic orientation) and grain sizes in the range of 0.26 millimeter to 0.38 millimeter. The ultrasonic transducer 22 used to obtain the histograms is a 15 megahertz spherical focalization transducer. The region for backscattering signal monitoring is specified by focusing the transducer on a flat bottom hole of 0.1 millimeter diameter located at a distance of two millimeters under the surface of the specimen material. Comparing FIG. 6 with FIG. 4, it may be seen that the less textured material of FIG. 6 exhibits a narrower and taller or more elongated histogram of backscattering signal amplitude than the material having more random texture as shown in FIG. 4. The X-ray diffraction pole-figures of FIGS. 5 and 7 confirm the findings of the observed differences in the preferred crystallographic orientations of the two specimen-materials. It should be noted that the effects of isolated, minute flaws on the histograms can be discarded or ignored if the total number of data points acquired exceeds the number of flaw-related data points by three to five orders of magnitude.

Figure 8:
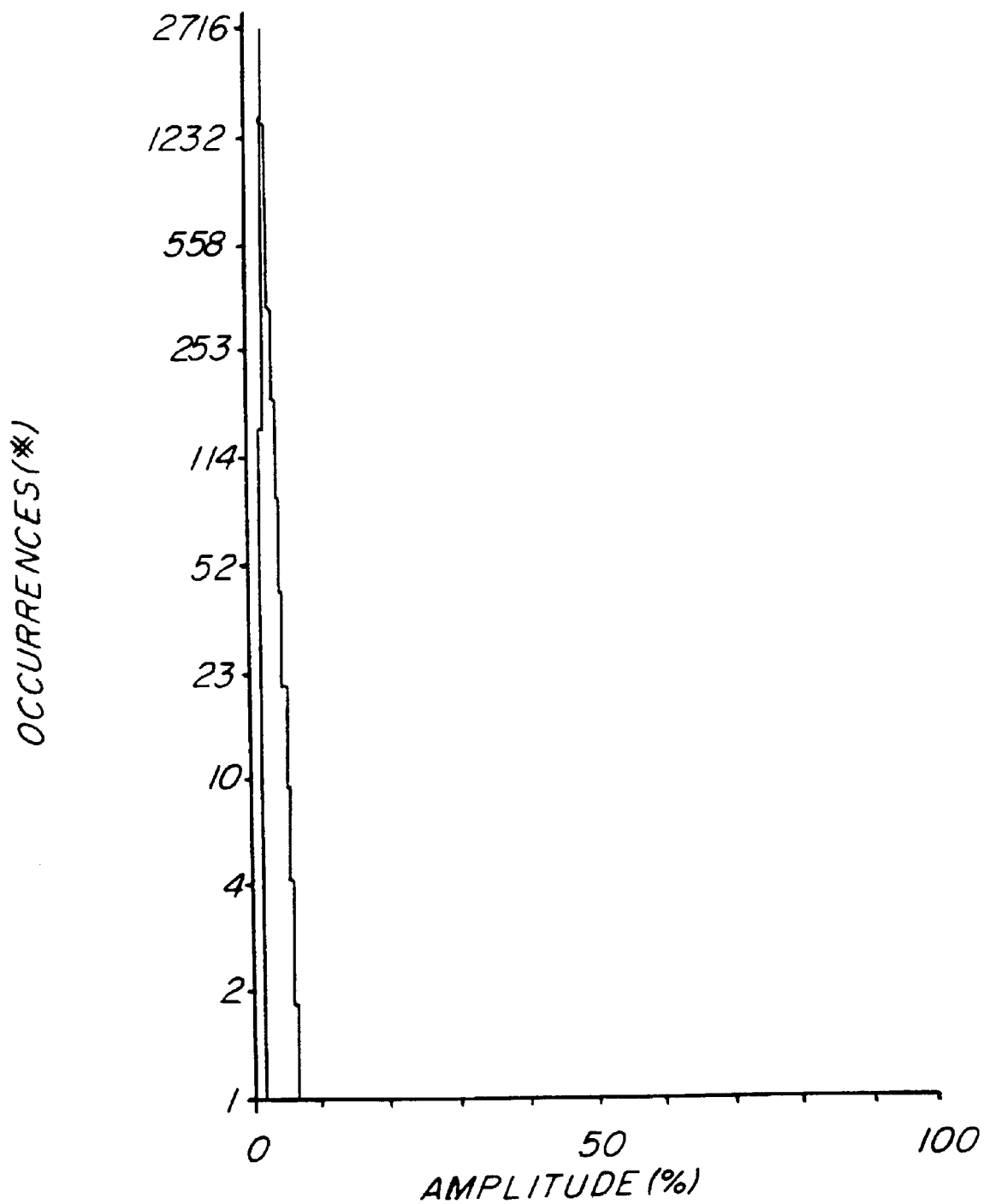
FIG. 8 is a histogram of "occurrences versus amplitude" obtained in accordance with the method of the invention for a <100> single crystal.

By way of comparison, the histogram for a single crystal of Al-0.5 wt % Cu alloy having a crystallographic orientation of <100> is shown in FIG. 8. The histogram of FIG. 8 was also obtained using a 15 megahertz spherical focalization transducer focused on a flat bottom hole of 0.1 millimeter diameter located at a distance of two millimeters beneath the surface of the crystal. The histogram shows an amplitude variation for the single crystal of about 4.7%, and a peak of about 2,716 occurrences.

Figure 9:
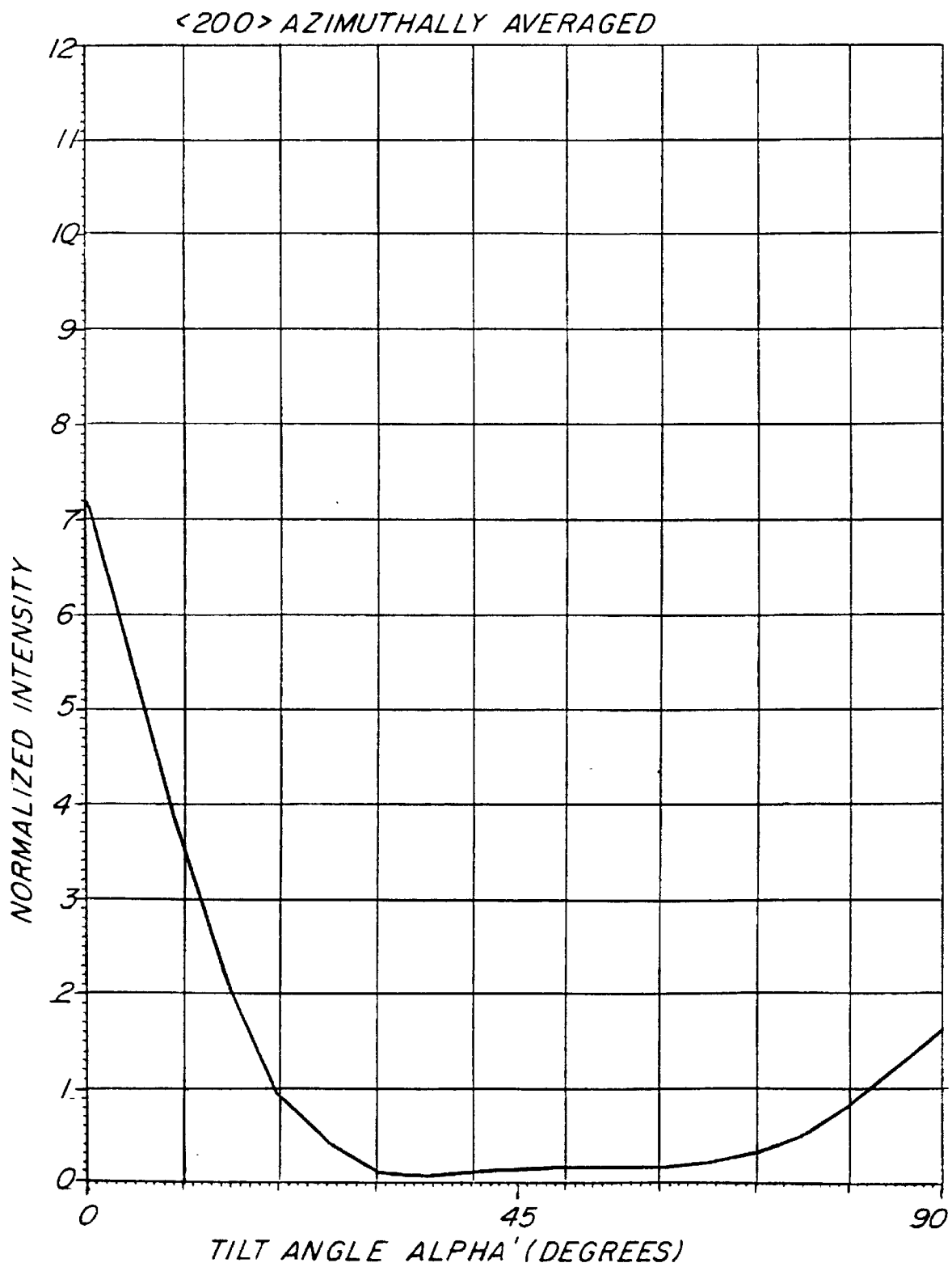
FIG. 9 is a plot of normalized intensity versus tilt angle alpha, <200> azimuthally averaged, for the sputtering target of FIGS. 4 and 5.
Figure 10:
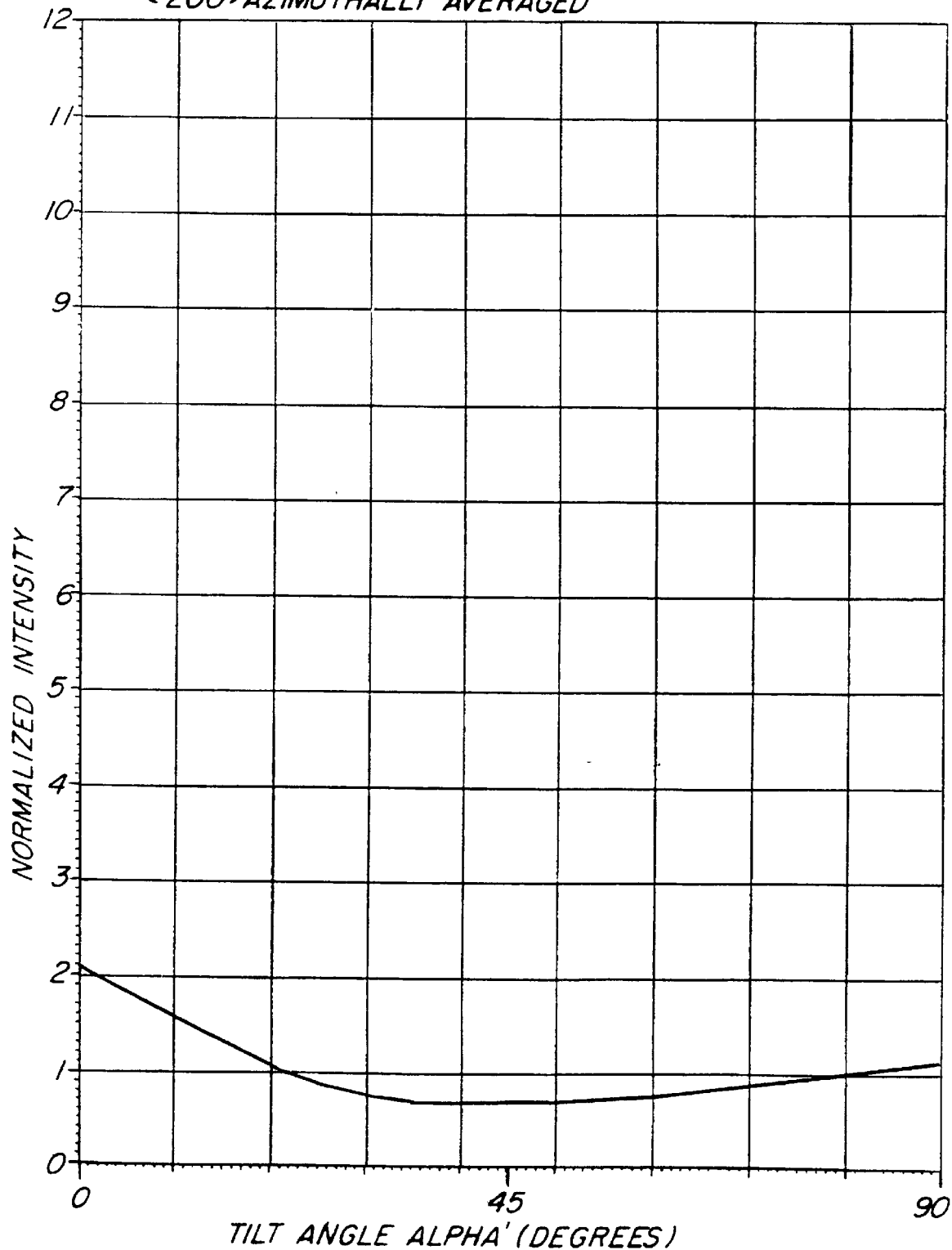
FIG. 10 is a plot of normalized intensity versus tilt angle alpha, <200> azimuthally averaged, for the sputtering target of FIGS. 6 and 7.
Figure 11:
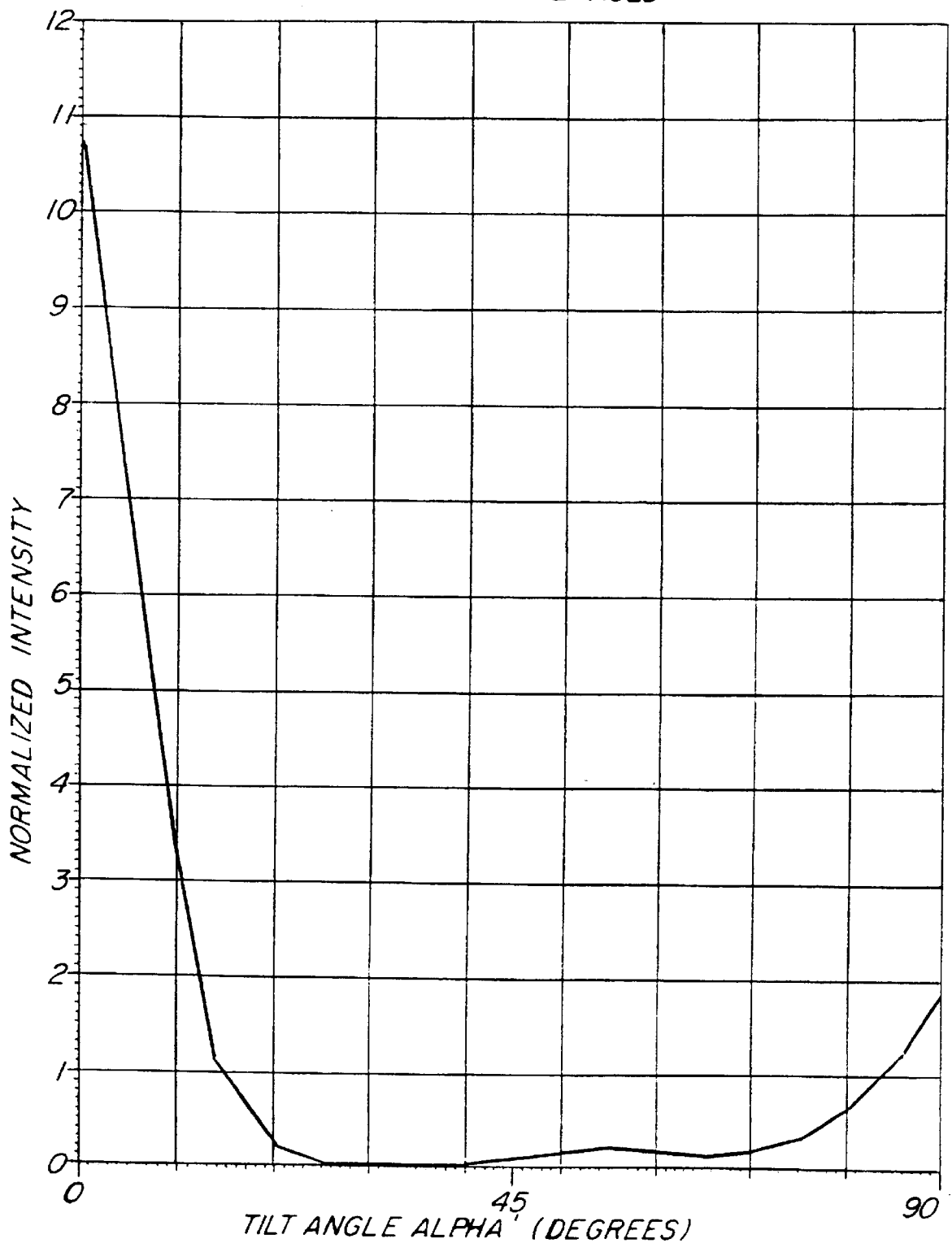
FIG. 11 is a plot of normalized intensity versus tilt angle alpha, <200> azimuthally averaged, for the <100> single crystal of FIG. 8.

Graphs of normalized intensity versus tilt angle alpha in degrees for a <200> azimuthally averaged X-ray beam for each of the samples of FIGS. 4, 6, and 8, may be seen in FIGS. 9, 10, and 11, respectively. FIG. 12 shows a plot of the normalized ultrasonic backscattering amplitudes versus the degree of preferred <200> intensity normalized (azimuthally averaged) for each of the three sample specimens.

The plot in FIG. 12 shows that there is a linear correlation between the results obtained from the instant texture characterization analysis by ultrasonic backscattering means and a conventional X-ray diffraction pole-figure analysis method. For example, point 202 in FIG. 12 shows the normalized intensities for both the ultrasonic detection means (y-axis) and x-ray diffraction methods (x-axis) as applied to the isotropic random texture specimen with point 204 representing the x, y coordinate intensities found for the strong <100> preferred orientation sample. Point 206 represents the ultrasonic and x-ray diffraction intensities for the single crystal material tested. Thus, the instant method of ultrasonic on-line texture characterization analysis yields good results when compared with standard out-of-line measurement techniques since there is a clear linear relationship between the two methods.

It is to be noted that the ultrasonic pulse to be applied to the sputter target may be applied through a fluid medium such as air or water. Presently, it is preferred to place the sample in a water immersion tank to thereby apply the pulse through water. Typically, the transducer will be located at normal incidence to the specimen surface.

The pulse or burst of MHz-range frequency electrical signal is generated by an electronic pulser tuned to the frequency range of the ultrasonic transducer (11-18.5 MHz). This signal is converted by the transducer into an ultrasound pulse. The ultrasound pulse propagates through the water (which is a couplant) at a normal incidence to the specimen surface.

As a result of the interaction of the ultrasonic pulse with the exposed volume of the specimen (approximately 5 mm deep into the specimen measured from the top surface) part of the ultrasonic energy is scattered back to the transducer in the form of an echo.

The exposed area is situated inside the transducer focal zone (−6 dB). When the echo arrives, the transducer electronically switches from an electronic transmitter to a gated electronic receiver. The echo is received at the transducer about 60 microseconds after the pulse is sent.

The returned RF signal (the ultrasonic echo) is captured inside the gate of a low noise gated preamplifier. The pre-amplified RF echo is passed to the low noise linear amplifier.

The echo acquisition system includes: the low noise gated preamplifier; the low noise linear amplifier with a set of calibrated attenuators; and a 12-bit ADC (2,44 mV/bit) and a PC equipped with a printer.

The linearly amplified analog RF echo signal is digitized by the 12-bit ADC (2, 44 mV/bit) and passed in digital form to the PC. The maximum value of the digitized RF signal is stored in the memory of the PC software. This maximum value is used for texture analysis.

The texture analysis device shown in FIG. 2 uses an immersion tank filled with DI water. It is equipped with a mechanical X-Y scanner, electronic pulser-receiver instrument and transducer assembly mechanically attached to the X-Y scanner. The mechanical X-Y scanner is controlled by a PC based electronic controller. The X-Y scanning unit performs a meander-like stepwise motion with short steps in the X direction and longer steps in the Y direction. Data acquisition steps in both X and Y directions were chosen to equal 0.8 mm to provide a detection of 0.1 mm flat bottom hole at detection level (9-6 dB) without exposure area overlapping.

The preferred transducer is sold by Panametrics, USA under the model V 319 designation. This is a high resolution piezoelectric transducer having a focalization distance of 51 mm and 12.5 mm in diameter with a center frequency of 15 MHz and 7.2 MHz bandwidth (-6 dB).

In detecting the backscatter echo, software available from Structural Diagnostics, Inc. under the designation SDI-5311 can be used.

Before testing, the specimen surface should be prepared via diamond cutting or the like. Usually, the texture characterization is performed for the entire area of the target, usually 7.5 in.×7.5 in. For texture analysis, about 50,000-500,000 raw data points are analyzed. The velocity of the ultrasonic pulses propagating from the target is commonly on the order of about $6.29$-$6.35 \times 10^{-1}$ cm/microsecond.

While the method herein described, and the form of apparatus for carrying this method into effect, constitutes a preferred embodiment of this invention, it is to be understood that the invention is not limited to this precise method and form of apparatus, and that changes may be made in either without departing from the scope of the invention, which is defined in the appended claims.

What is claimed is:

1. A method of non-destructively testing a sputtering target having a front wall and comprising sputtering material having grain boundaries and an approximately known grain size, said method comprising the steps of:

(1) directing a pulsed beam of sonic energy from a transmission point toward said target, said sonic energy having a frequency such that its wavelength in said target is substantially equal to said known grain diameter and said beam being directed such that a portion thereof passes through said front wall, reflects off said grain boundaries, passes again through said front wall and travels to a reception point having a predetermined position relative to said transmission point;

(2) sensing said beam portion at said reception point and generating a corresponding sensing signal; and (3) determining for said sensing signal a histogram of the number of occurrences of said sensing signal at a predetermined amplitude level.

2. A method of determining the degree of preferred crystallographic orientation of a sputtering target having an approximately known nominal grain size and grain boundaries comprising the steps of:

(a) irradiating said sputtering target with an ultrasonic pulse having a wavelength, in the sputtering target, in the range of said nominal grain size of said sputtering target;

(b) detecting backscattering echoes generated by said ultrasonic pulse interacting with said grain boundaries in said sputtering target;

(c) generating an electrical signal representative of said detected backscattering echoes;

(d) determining the number of occurrences of said detected backscattering echoes for predetermined ranges of amplitudes of said detected backscattering echoes;

(e) producing a histogram of said number of occurrences versus said predetermined ranges of amplitudes for said sputtering target; and (f) comparing said histogram with reference histograms for reference sputtering targets having known preferred-crystaliographic orientations.

3. An express ultrasonic method for on-line texture characterization which provides a control for the texture variation in production environment, consists of a pulse-echo method incorporated into an ultrasonic C-scanning process, wherein a megacycle center frequency ultrasonic pulse generated by a broad-band focused ultrasonic transducer is introduced at a normal incidence into material wherein the ultrasonic signal due to an interaction with material texture scatters back to the transducer in the form of a backscattering echo which is further converted by the transducer into an electrical signal and processed by a broad-band acquisition system, extracting and storing the backscattering signal amplitude, the distinct form of this method comprising:

(a) the generation of the initial ultrasonic pulse with a wavelength in the range of the average grain size in the direction of ultrasound propagation;

(b) the backscattering signal is collected from the region of several grain layers thick located inside the transducer focal zone;

(c) the backscattering signal is collected from the region located at the distance, at least, of one grain layer underneath the surface.

4. The method as in claim 3 wherein said amplitude of said backscattering signal is graphically treated in a form of histogram as occurrences versus amplitude where the amplitude is plotted along the X-axis while the occurrences—along the Y-axis.

5. A method for non-destructively testing a sputter target, said method comprising the steps of:

(a) directing a mechanical wave normally onto a surface of said sputter target, said mechanical wave including a component having a selected wavelength in the sputter target on the order of an average grain size of said target;

(b) detecting backscattered waves from said target having said selected frequencies;

(c) relating amplitudes of the backscattered waves with detected occurrences of said backscattered waves having said amplitudes so as to obtain a characterization of a grain texture of said sputter target.

6. The method as recited in claim 5 wherein said step (c) includes generating a digital electrical signal relating said amplitudes with said detected occurrences.

* * * * *